(12) United States Patent
Kolahi (10) Patent No.: US 7,134,348 B2
(45) Date of Patent: Nov. 14, 2006

(54) METHOD FOR OPERATING A MASS FLOWMETER

(75) Inventor: Kourosh Kolahi, Kiel (DE)

(73) Assignee: Krohne AG, Basel (CH)

( * ) Notice: Subject to any disclaimer, the term of this patent is extended or adjusted under 35 U.S.C. 154(b) by 0 days.

(21) Appl. No.: 11/284,369

(22) Filed: Nov. 21, 2005

(65) Prior Publication Data

US 2006/0107759 A1 May 25, 2006

(30) Foreign Application Priority Data

Nov. 23, 2004 (DE) .................... 10 2004 056 555
Mar. 23, 2005 (DE) .................... 10 2005 014 058

(51) Int. Cl.
*G01F 1/84* (2006.01)
(52) U.S. Cl. ................................. 73/861.355
(58) Field of Classification Search .......... 73/861.355, 73/861.356, 861.357
See application file for complete search history.

(56) References Cited

U.S. PATENT DOCUMENTS 5,359,881 A * 11/1994 Kalotay et al. ............ 73/54.06
5,373,745 A 12/1994 Cage
5,423,225 A * 6/1995 Cage ...................... 73/861.356
5,448,921 A 9/1995 Cage et al.
5,473,949 A 12/1995 Cage et al.
5,497,665 A 3/1996 Cage et al.
5,576,500 A 11/1996 Cage et al.
5,861,561 A * 1/1999 Van Cleve et al. ...... 73/861.52
6,763,730 B1 7/2004 Wray

OTHER PUBLICATIONS

Prof. Dr. Sc. Nat Otto Fielder, Stromungs—und Durchflussmesstechnik, R. Oldenbourg Verlag GmbH, 1992, München.

* cited by examiner

*Primary Examiner*—Jewel Thompson
(74) *Attorney, Agent, or Firm*—Cesari and McKenna, LLP; John F. McKenna (57) ABSTRACT

A method for operating a Coriolis mass flowmeter incorporates a measuring tube through which flows a medium and which is stimulated into oscillating at a minimum of one frequency, the resulting oscillations of the measuring tube being detected and measured. The viscosity of the medium flowing through the measuring tube is determined as a function of the pressure drop along the measuring tube, thus permitting a precise determination of the viscosity in simple and reliable fashion.

16 Claims, 6 Drawing Sheets

METHOD FOR OPERATING A MASS FLOWMETER

BACKGROUND OF THE INVENTION

1. Field of the Invention

This invention relates to a method for operating a mass flowmeter that employs the Coriolis principle and encompasses a measuring tube through which flows a medium and which is stimulated into oscillating at a minimum of one frequency, allowing the resulting oscillations to be detected and measured.

2. The Prior Art

Coriolis mass flowmeters operated by the method referred to above have been well known in the prior art, as described for instance in DE 100 02 635 A1. Conventional Coriolis mass flowmeters often employ natural self-resonance, i.e. they are energized at a self-resonant frequency—also referred to as the natural frequency—of the measuring tube. A change in the natural frequency of the measuring tube through which flows a medium relative to the natural frequency of an empty measuring tube provides an indication of the density of the flowing medium. Another variable of interest is the viscosity of the medium flowing through the measuring tube.

In conventional Coriolis mass flowmeters, one approach, described for instance in DE 100 20 606 A1, has been to generate torsional vibrations of the measuring tube and to measure the viscosity by determining the amount of increased energy consumption brought about by the shearing strain bearing on the medium. That method, however, is susceptible to certain deficiencies which considerably compromise accurate viscosity determinations.

SUMMARY OF THE INVENTION

It is, therefore, the objective of this invention to introduce a method for operating a Coriolis mass flowmeter that permits measuring the viscosity of the medium flowing through the measuring tube independent of the energy consumption of the Coriolis mass flowmeter.

In terms of the method referred to further above, this objective is achieved in that the viscosity of the medium flowing through the measuring tube is measured on the basis of the pressure drop along the measuring tube.

The fundamental concept on which this invention is based thus consists in an indirect determination of the viscosity by way of the pressure drop of the medium along the measuring tube, without taking into account any change in the energy consumption. According to one preferred embodiment of the invention, it is in fact possible to derive the pressure-drop determination along the measuring tube from the dynamic pressure by means of the formula $$\Delta p = C_W \cdot p_S \frac{L}{d}, \tag{1}$$

where $\Delta p$ represents the pressure drop along the measuring tube, $C_W$ is the coefficient of friction as a function of $64/Re$ with a Reynolds' number $Re$, $p_S$ is the dynamic pressure, $L$ is the length of the measuring tube and $d$ is the diameter of the measuring tube.

In a preferred embodiment of the invention, the dynamic pressure $p_S$ is indirectly determined via the mean velocity $\overline{v}$ of the flowing medium, preferably by applying the equation $$p_S = \frac{1}{2} \rho \cdot \overline{v}, \tag{2}$$

where $\rho$ represents the density of the medium. The mean velocity is arrived at by $$\overline{v} = \frac{\dot{m}}{A \cdot \rho}, \tag{3}$$

where A represents the traversed cross-sectional area of the measuring tube.

A preferred, enhanced embodiment of the invention establishes the mathematical correlation between the coefficient of friction $C_W$ and the Reynolds' number Re for determining the viscosity of the medium flowing through the measuring tube, with that value preferably stored in a suitable memory module of the Coriolis mass flowmeter.

A preferred embodiment of the invention also provides for the viscosity of the flowing medium to be determined via the formula $$\eta = \frac{\overline{v} \rho d}{Re} \tag{4}$$

which is arrived at by defining the Reynolds' number:

$$Re = \frac{\overline{v} \rho d}{\eta} \tag{5}$$

The differential pressure of the medium flowing through the measuring tube can be determined by essentially any known differential-pressure measuring process. In a preferred embodiment of the invention, however, the pressure drop along the measuring tube is quantified in that the collected oscillations of the measuring tube are evaluated on the basis of a physical-mathematical model for the dynamics of the mass flowmeter.

It is particularly desirable for the physical-mathematical model to be capable of describing the oscillations of the mass flowmeter upon stimulation of the measuring tube in its first natural mode and/or in its second natural mode. A preferred embodiment of the invention provides for the physical-mathematical model to take into account the coupling between the first and the second natural modes of the oscillations of the measuring tube. The determination of the viscosity is thus possible based on the pressure drop via the coupling between the two natural modes at one or several frequencies, preferably at the resonant frequency of the first natural mode.

A preferred embodiment of the invention also provides for the physical-mathematical model to take into account, apart from the measuring tube, the effect of at least one other component of the mass flowmeter, such as a support pipe and/or a suspension of the measuring tube in the mass flowmeter. In addition, or as an alternative, a preferred embodiment of the invention includes the measurement of the temperature in the mass flowmeter so as to take into account the temperature dependence of the functional performance of components of the mass flowmeter such as an oscillation generator for the measuring tube and/or an oscillation sensor for the measuring tube. A preferred embodiment of the invention further provides for measuring the temperature of the measuring tube so as to take into account temperature-related changes in the geometry of the measuring tube. In addition, a preferred implementation of the invention takes into account a pressure-related change in the geometry of the measuring tube by gauging the pressure in the measuring tube.

There are numerous ways in which the method according to this invention can be configured and further enhanced. In that context, attention is invited to the dependent claims, and to the following description of a preferred invention embodiment with reference to the drawings.

The viscosity of a medium, also called viscousness, is the tendency of the medium to resist the movement of two mutually adjoining layers of the medium relative to each other, a phenomenon also referred to as internal friction. The resulting flow resistance is encountered not only with liquids but with gases and indeed solids as well. The dynamic viscosity $\eta$ is described as the proportionality factor between shearing strain and friction velocity, i.e. the shear rate of the flow. Dividing the dynamic viscosity by the density of the medium provides the kinematic viscosity.

Figure 1:
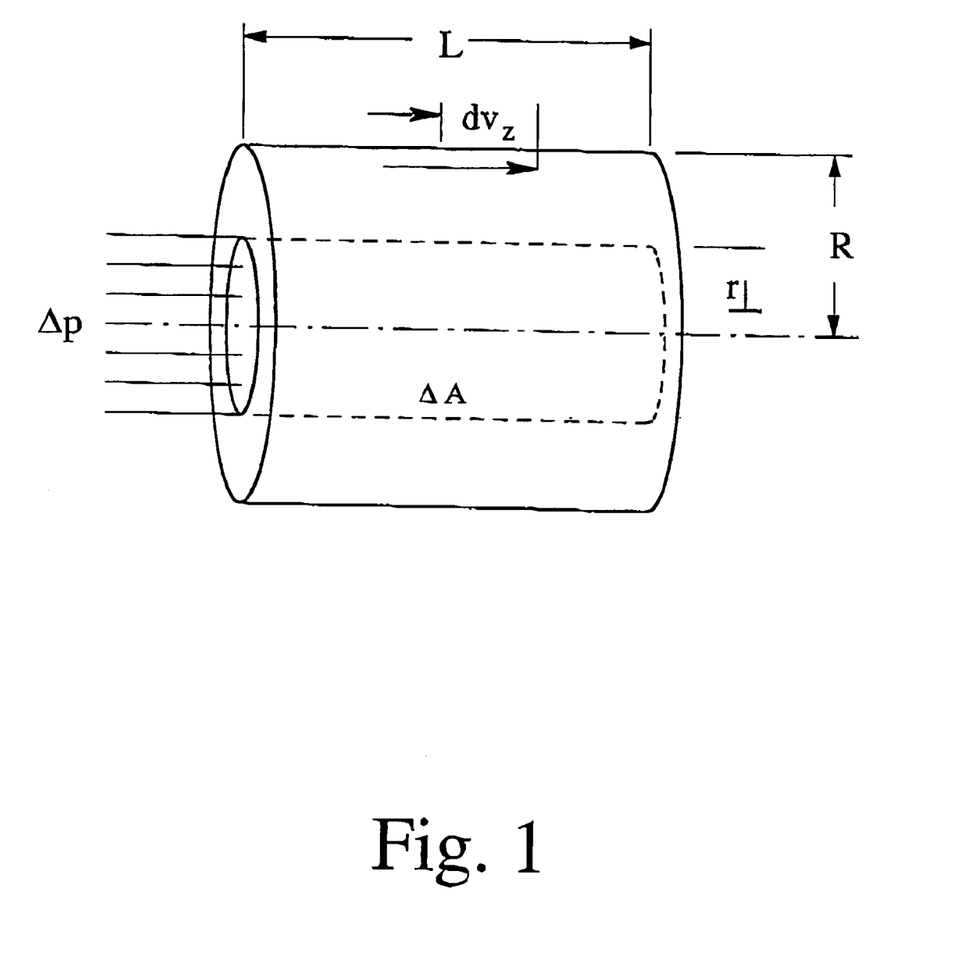
FIG. 1 is a schematic illustration of the friction at the interface of neighboring flow segments of the medium flowing through the measuring tube of a Coriolis mass flowmeter.

FIG. 1 is a schematic illustration of the surface friction between two mutually adjoining laminar-flow segments. In the case of a laminar flow, there exists an equilibrium in the flow direction between the frictional force $F_w$ mutually exerted by neighboring flow segments $\Delta A$ at respectively different velocity rates and the force of pressure F that pushes the segments past each other:

$$F_W = \eta \frac{dv_Z}{dr_\perp} \cdot \Delta A, \tag{6}$$

where $dv_2/dr_\perp$ describes the velocity gradient between the flow segments while the following represents the force of pressure F:

$$F = \Delta p \cdot \pi r_\perp^2. \tag{7}$$

The result is a differential equation for the velocity profile:

$$\frac{dv_Z}{dr_\perp} = \frac{r_\perp}{2\eta} \cdot \frac{\Delta p}{L} \tag{8}$$

the solution being $$v_2 = \frac{1}{4\eta}(R^2 - (r_\perp)^2) \cdot \frac{\Delta p}{L}, \tag{9}$$

where R represents the radius of the measuring tube. This flow profile is a paraboloid with the following peak values:

$$v_Z(r_\perp = 0) = \frac{R^2}{4\eta} \cdot \frac{\Delta p}{L} \text{ and } v_Z(r_\perp = R) = 0. \tag{10}$$

Consequently, the pressure p bearing on the inner liquid cylinder pushes the latter through the outer cylinder with a velocity difference of $dv_2$, thus generating the frictional force $F_w$ at the interface $\Delta A$.

Figure 2:
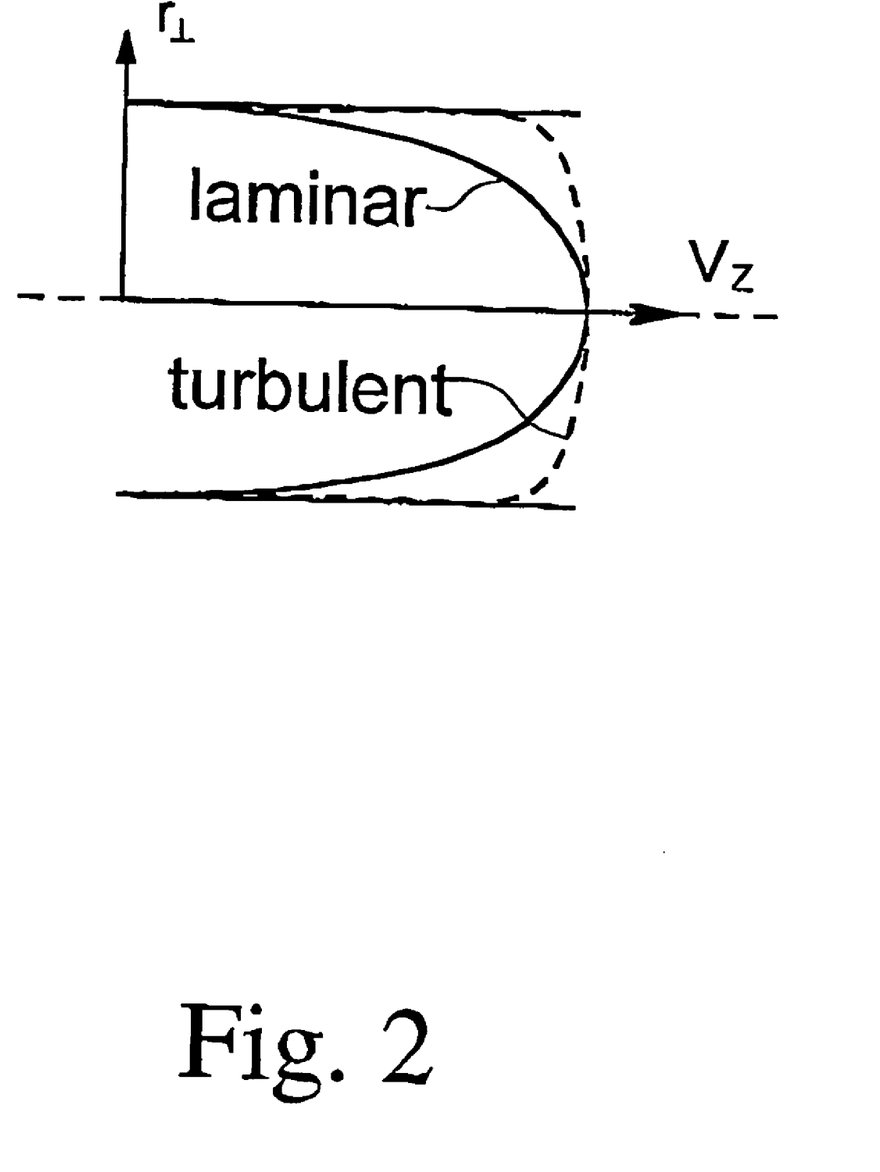
FIG. 2 shows the flow pattern in the case of a laminar and, respectively, turbulent flow.

The resulting velocity profile for a laminar flow is schematically illustrated in FIG. 2. For comparative purposes, the flow pattern of a turbulent flow is shown as well, its salient feature being that the flow velocity changes little in the inner region while diminishing sharply only near the wall of the measuring tube.

It is now possible to determine the mass carried through the measuring tube per unit of time as follows:

$$\dot{m} = \frac{dm}{dt} = 2\pi\rho \int_0^P v_Z(r_\perp)r_\perp dr_\perp = \frac{\pi}{8}\frac{\rho}{\eta}R^4\frac{\Delta p}{L}. \tag{11}$$

This corresponds to Hagen-Poiseuille's established formula that describes the interrelationship between mass flow, fluid density and dynamic viscosity in a laminar flow.

Given that in a Coriolis mass flowmeter the flow is mostly turbulent, the effect of vis inertiae must be factored in. It is important to know how much energy $\Delta W$ is needed to transport the mass $\Delta m$ over the length L of the measuring tube. This relationship is derived as shown below:

$$\frac{\Delta W}{\Delta m} = \frac{\Delta p \pi R^2 L}{\rho \pi R^2 L} = \frac{\Delta p}{\rho}, \tag{12}$$

where for a laminar flow the following applies:

$$\Delta p = \frac{8L\eta \dot{m}}{\pi R^4 \rho}. \tag{13}$$

When, in this equation, $\dot{m}$ is calculated as a function of $$\dot{m} = \pi R^2 \rho \bar{v} \tag{14}$$

based on the mean flow velocity $\bar{v}$, the result will be $$\Delta p = \frac{8L\eta\bar{v}}{R^2}. \quad (15)$$

If this equation includes the ratio between the frictional forces and the vis inertiae, i.e. the Reynold's number, $$Re = \frac{2R\bar{v}\rho}{\eta} \quad (16)$$

the result will be $$\Delta p = \frac{64}{Re} \cdot \frac{\rho \bar{v}^2}{2} \cdot \frac{L}{d}. \quad (17)$$

The variable $$P_S = \frac{\rho \bar{v}^2}{2} \quad (18)$$

is generally referred to as dynamic pressure and $64/Re = C_w$ as the coefficient of friction of the flow. The result will thus be $$\frac{\Delta w}{\Delta m} = c_w \frac{P_S L}{\rho d} = \frac{\Delta p}{\rho}. \quad (19)$$

This formulation, initially employed for laminar flows only, is universally applicable, i.e. for turbulent flows as well, for as long as the correct value for the coefficient of friction is used. In this case:

$C_w = 64/Re$ for laminar flows and $C_w >> 64/Re$ for turbulent flows.

Figure 3:
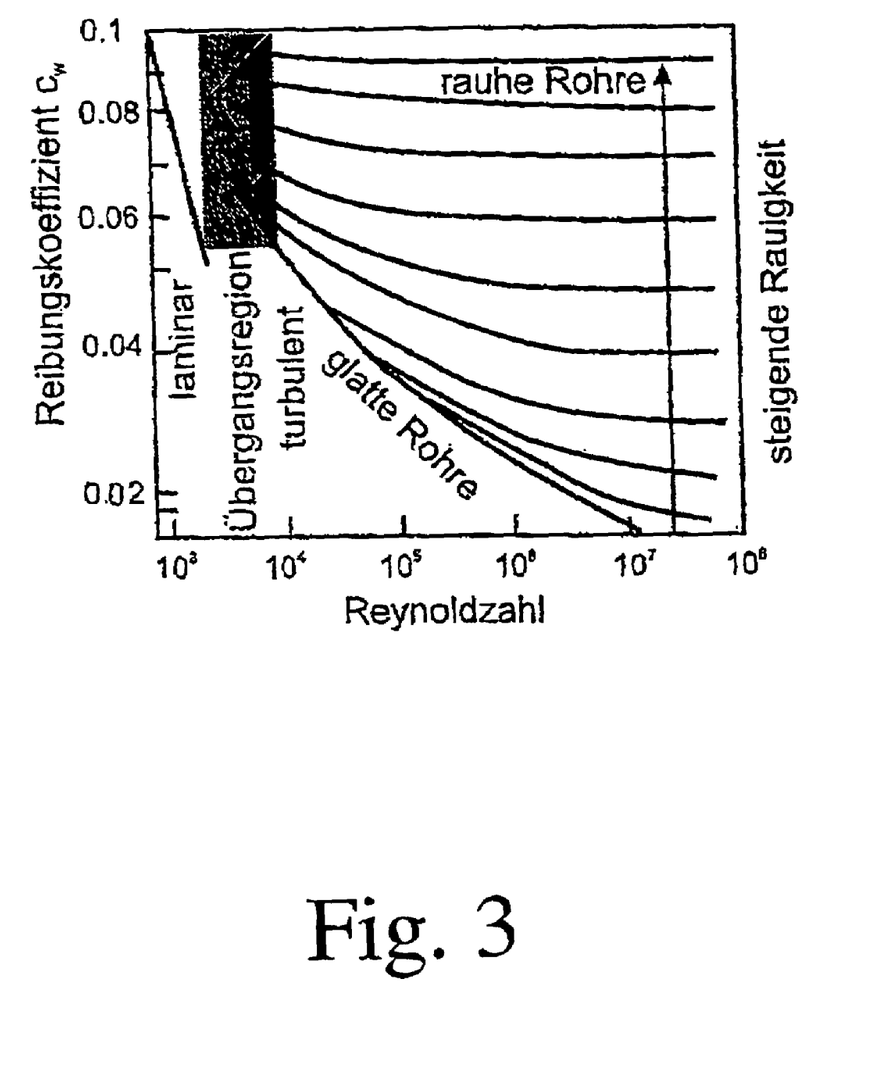
FIG. 3 shows the coefficient of friction as a function of the Reynolds' number for laminar and, respectively, turbulent flows.

FIG. 3 illustrates schematically the dependence of the coefficient of friction on the Reynolds' number. For very large Reynolds' numbers, $C_w$ is practically constant, except that it depends on the surface condition of the wall of the measuring tube, i.e. on its relative surface roughness. In a Coriolis mass flowmeter with a measuring tube diameter for instance of 10 mm, the Reynolds' number for a typical nominal flow rate will be about $Re = 10^5$, affording sufficient sensitivity between the coefficient of friction $C_w$ and the Reynolds' number. For viscosity measurements, this permits the determination first of the coefficient of friction $C_w$ and then of the associated Reynolds' number by applying the memory-stored correlation with the coefficient of friction, followed by the determination of the viscosity via the equation $$\eta = \frac{2R\bar{v}\rho}{Re} \quad (20)$$

The density $\rho$ can be measured by any popular method. The mean velocity $\bar{v}$ as well can be determined by any known process. In the case here described, this determination is preferably made in accordance with Equation 14 as indicated below:

$$\bar{v} = \frac{\dot{m}}{\pi R^2 \rho}. \quad (21)$$

For determining the relationship between the coefficient of friction and the associated Reynolds' numbers, the values for $C_w$ are recorded at different flow rates, for instance of water. That relationship can be quite closely approximated by means of a mathematical matrix with only few parameters.

As has been stated above, the differential-pressure measurement can be performed by any traditional procedure such as pressure gauging by means of wire strain-gauge extensometers. A preferred embodiment of the invention, however, employs a model-based method.

In this model-aided approach, the measuring tube functions as a resilient element subjected at its input and output ends to different pressures. Accordingly, the intake half of the measuring tube and the outlet half of the measuring tube display mutually different spring constants, resulting in an asymmetric condition in the measuring tube. This asymmetry leads to a coupling $K_{sij}$, proportional to the excursion rate, of the natural modes of the measuring tube. These exhibit an orthogonal pattern relative to the proportionally velocity- and mass-flow-dependent coupling of the natural modes. It allows the differential pressure to be measured, for instance, via the real component of the oscillations of the second natural mode when, as is often done with Coriolis mass flowmeters, the first natural mode is stimulated at its resonant frequency.

Figure 4:
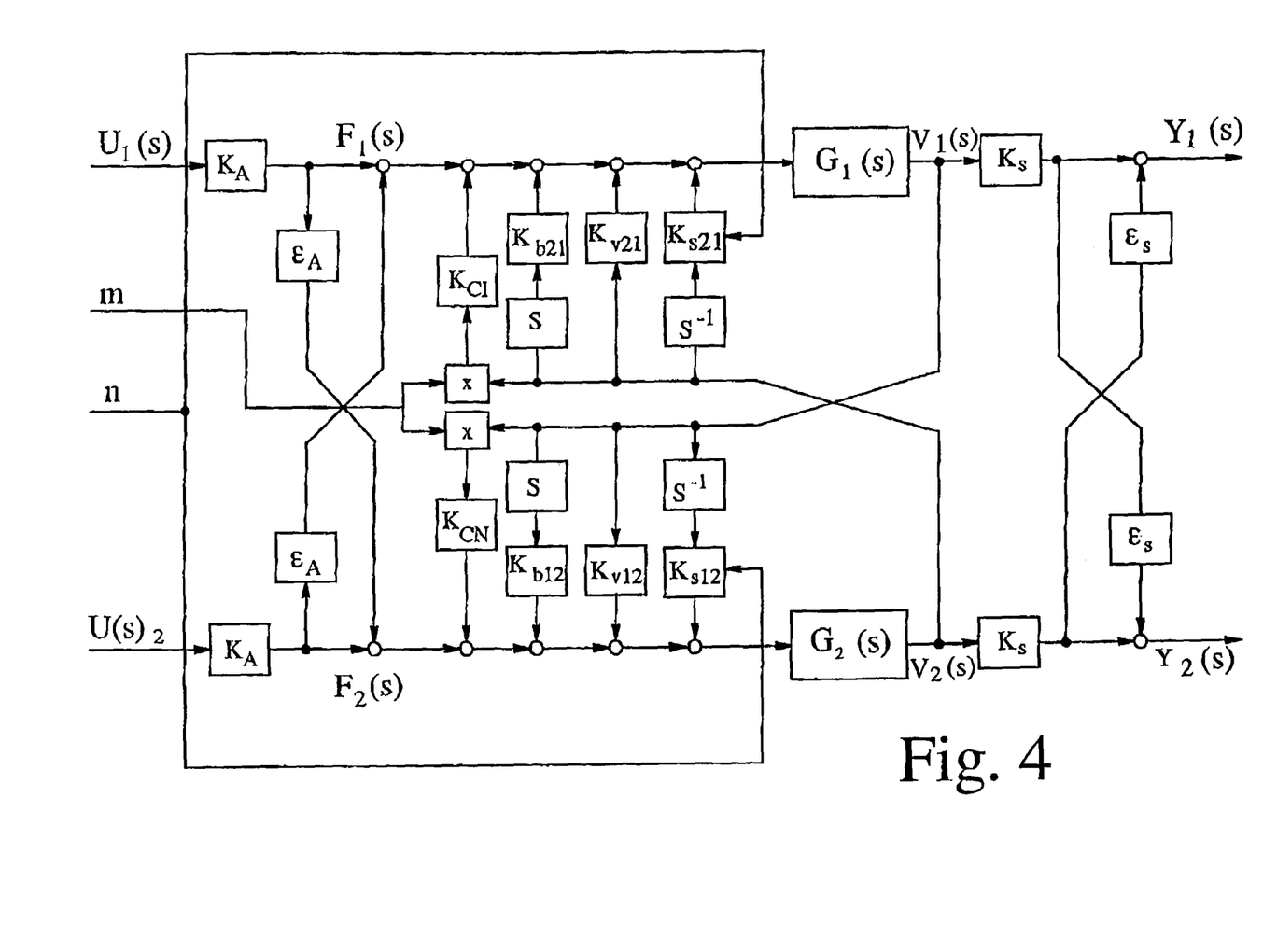
FIG. 4 depicts the structural layout of a physical-mathematical model for describing the dynamics of a Coriolis mass flowmeter.

FIG. 4 shows the effect of the viscosity as reflected in the physical-mathematical model employed in this case for the dynamics of the Coriolis mass flowmeter. Those skilled in the art know how to measure the $K_{sij}$ in which connection, reference is made to DE 100 02 635 A1.

The differential pressure can be measured by any traditional procedure such as pressure gauging by means of wire strain-gage extensometers. The preferred method, however, is described below. It utilizes two physically different effects:

1. Changed spring constant of the two halves of the measuring tube: the first effect sees the measuring tube as a resilient element exposed at its input and output ends to mutually different pressures. Consequently, the spring constant at the intake end differs from that at the outlet end, the result being an asymmetry in the measuring tube 1. For the model with discrete substitute elements, described further below in reference to FIG. 6, this means that the concentrated substitute resilient rigidity values are unevenly modified by the differential pressure ($C_{Ma} \neq C_{Mb}$). Their difference $k_s = C_{Ma} - C_{Mb}$ is a measure of the differential pressure in the measuring tube: $k_s = f(\Delta p)$. This asymmetry of the spring constants leads to excursion-proportional couplings $k_{sij}$ of the natural modes of the measuring tube 1.

2. Changed masses in the halves of the measuring tube: in the case of the second effect, the differential pressure compresses the compressible phase, if there is one, at a rate that differs between the input and output halves of the measuring tube. Consequently, the intake and outlet halves of the measuring tube exhibit different mass values, leading to an asymmetry in the measuring tube. For the model with discrete substitute elements described further below in reference to FIG. 6, this means that the concentrated substitute masses are unevenly modified by the differential pressure ($m_{Ma} \neq m_{Mb}$). Their difference $k_a = m_{Ma} - m_{Mb}$ is a measure of the differential pressure in the measuring tube, assuming a flow phase is compressible: $k_a = f(\Delta p)$. This asymmetry leads to acceleration-proportional couplings $k_{aij}$ of the natural modes of the measuring tube.

The couplings, as a proportional function of the excursion and acceleration rates, are not mutually distinguishable in the case of single-frequency operation since in their resonant state their effect is identical. Determining their combined effect does not require a separate quantification of $k_{sij}$ and $k_{aij}$; instead, one of their combinations shown below can easily be quantified in the resonant state:

$$k_{saij}(s) = k_{aij}s^2 + k_{sij} \text{ and specifically for} \quad (22)$$
$$k_{sa12}(s) = k_{a12}s^2 + k_{s12}$$

$$k_{asij}(s) = k_{aij} + \frac{k_{sij}}{s^2} \text{ and specifically for} \quad (23)$$
$$k_{as12}(s) = k_{a12} + \frac{k_{s12}}{s^2},$$

where s is the Laplace operator. The following relation exists between the equivalent coefficients:

$$\frac{k_{as12}(s)}{k_{sa12}(s)} = \frac{1}{s^2}. \quad (24)$$

When the frequency is known, the equivalent coefficients can be mutually correlated.

FIG. 4 illustrates examples of the couplings of the first natural mode with the second natural mode, purely as excursion-proportional couplings $k_{sa12}$ and $k_{sa21}$, in terms of the difference in the respective resilient rigidity and mass.

In that block diagram:
$\Delta p$:=the differential pressure in the measuring tube,
$\dot{m}$:=the mass flow,
$F_1(s)$:=the excitation force in the area shown for the first natural mode,
$V_1(s)$:=the velocity signal in the area shown for the first natural mode,
$G_1(s)$:=the transfer function of the first natural mode,
$k_{sa12}$:=the excursion-proportional coupling from the first to the second natural mode,
$F_2(s)$:=the excitation force in the area shown for the second natural mode,
$V_2(s)$:=the velocity signal in the area shown for the second natural mode,
$G_2(s)$:=the transfer function of the second natural mode,
$k_{sa21}$:=the excursion-proportional coupling from the second to the first natural mode,
$K_{CN}$:=the mass-flow-dependent (velocity-proportional) coupling from the first to the second natural mode,
$K_{C1}$:=the mass-flow-dependent (velocity-proportional) coupling from the second natural mode to the second [sic] natural mode, and S:=the Laplace operator ($S^{-1}$ signifies that the passing signal is phase-shifted by $-90°$).

The excursion-proportional couplings via $k_{sa21}$ and $k_{sa12}$ are orthogonal relative to the mass-flow-dependent (velocity-proportional) coupling of the natural modes via $K_{CN}$ and $K_{C1}$. In essence, this means a separation of the mass-flow-dependent and differential-pressure-dependent oscillations of the natural modes.

The couplings $k_{saij}$ can be identified by different methods. For example, the coupling $k_{sa12}$ can be determined by the following relation:

$$k_{sa12} = \frac{\omega_{01} \text{Re}\{V_2(\omega_{01})\}}{\text{Re}\{V_1(\omega_{01})\}\text{Im}\{G_2(\omega_{01})\}} \quad (25)$$

In this equation, the symbols represent the following:
$k_{a12}$:=the difference between the resilient rigidity values and between the mass values of the measuring tube halves $C_{Ma} - C_{Mb}$,
$\omega_{01}$:=the resonant frequency of the first natural mode,
$\text{Re}\{V_1(\omega_{01})\}$:=the real component of the velocity signal of the first natural mode,
$\text{Re}\{V_2(\omega_{01})\}$:=the real component of the velocity signal of the second natural mode, and
$\text{Im}\{G_2(\omega_{01})\}$:=the imaginary component of the transfer function of the second natural mode.

The conditional equation (Equation 25) is based on the assumption that
1. the measuring tube oscillates at the resonant frequency of the first natural mode $\omega_{01}$, and
2. the real component of the transfer function of the second mode equals zero ($\text{Re}\{G_2(\omega_{01})\}=0$), i.e. that at this frequency the second natural mode acts as a spring whose spring constant is known.

The difference between the resilient rigidity values and between the mass values $k_{sa12}$, and thus the differential pressure as well, can be determined by a compensatory process independent of a possibly changing imaginary component of the transfer function of the second mode. To that effect, the measured variable $\text{Re}\{V_2(\omega w_{01})\}$ is adjusted to zero in a control circuit via the stimulation of the second natural mode employing the excitation force $F_2$. This adjustment, also reflected in FIG. 4, forces the condition where $F_{2k} = F_{s12}$. Thus, $k_{sa12}$ can be quantified as a measure for the differential pressure via the conditional equation $$k_{sa12} = -\frac{\omega_{01} F_{2K}(\omega_{01})}{\text{Re}\{V_1(\omega_{01})\}} \quad (26)$$

At this juncture, it is important to note that the two effects, i.e. the differential-pressure-dependent resilient rigidity changes of the measuring tube halves and the differential-pressure-dependent mass changes of the measuring tube halves may be utilized in other preferred embodiments, individually and separately or in other combinations, for the purpose of differential pressure measurements.

The pressure drop in the measuring tube can be calculated on the basis of the measured couplings $k_{saij}$, where in the simplest approach to a mode $$\Delta p = K_{pij} + K_{saij} + K_{pijo}, \text{ and specifically for } K_{sa12} \quad (27)$$

$$\Delta p = K_{p12} k_{sa12} + K_{p120} \quad (28)$$

The parameters of this version and perhaps other versions of a model can easily be predetermined in a calibration of the mass flowmeter and suitably saved in a memory module. It is not always necessary to define them, however, since $k_{saij}$, constituting a quantifier for $\Delta p$, is first broken down into its direct and alternating components. The direct component is used as a measure for the viscosity and the alternating component as a measure for determining the multiphase flow.

DESCRIPTION OF AN ILLUSTRATIVE EMBODIMENT

Figure 5:
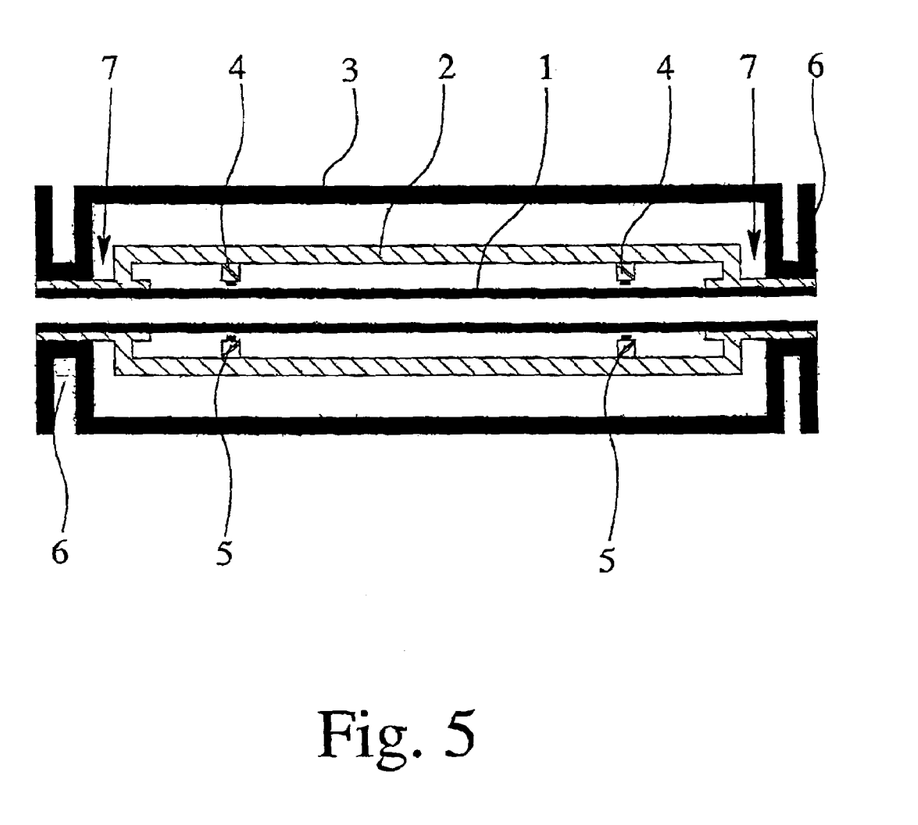
FIG. 5 illustrates the mechanical configuration of a Coriolis mass flowmeter for use in conjunction with a preferred embodiment of the invention.

FIG. 5 is a sectional view of a Coriolis mass flowmeter for operation by the method here described as a preferred embodiment of the invention. The Coriolis mass flowmeter incorporates a measuring tube 1, a support pipe 2, a protective tubular casing 3, two oscillation generators 4 and two oscillation sensors 5. One single linear measuring tube 1 is provided, permitting installation in a pipeline system, not illustrated, via flanges 6. The measuring tube 1 and the support pipe 2 are connected between the flanges and the system by way of suspension elements referred to as mounts 7. Additionally provided in the center of the measuring tube 1, connecting the measuring tube 1 with the support pipe 2, is a central spring 8 that serves to augment the stiffness of the measuring tube 1, as described for instance in DE 42 00 060 A1. It should be noted that the invention is not limited to the configuration depicted in FIG. 1, but can be used with essentially any tube geometry including a dual-tube design.

Figure 6:
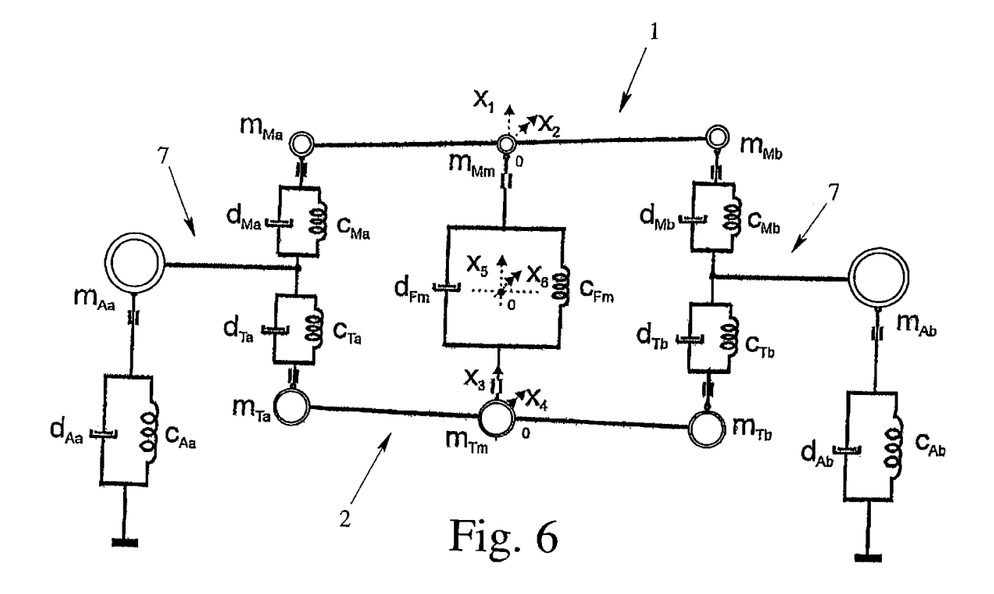
FIG. 6 shows a design approach used for the physical-mathematical model, with concentrated substitute elements.

FIG. 6 shows a physical-mathematical model, used for the invention embodiment here described, with concentrated substitute elements of the Coriolis mass flowmeter. The significant mechanical movements of the Coriolis mass flowmeter, indicated in FIG. 5, consist of the oscillations of the measuring tube 1 and of the support pipe 2 in their first natural mode and, respectively, their second natural mode. They can be described with the aid of the oscillation pattern of the model shown in FIG. 6. The substitute elements marked M describe the effective masses, springs and attenuators of the measuring tube 1, the elements marked T describe those of the support pipe 2. The substitute elements marked A describe the masses, springs and attenuators of the mounts 7. The indices a and b represent the left and, respectively, right half of the measuring tube 1, the support pipe 2 and the mounts 7. The spring and attenuator Fm are so located as to permit the measuring tube 1 to be maintained in a center position by the central spring 8. Of course, if no central spring is provided, the corresponding references do not apply. The masses marked m reflect the fact that the oscillations in the first natural mode of the measuring tube and the support pipe involve a larger mass than do the oscillations in the second natural mode.

In this model, an oscillation in the first natural mode reflects the cophasal translational movement of the masses of the measuring tube 1, the support pipe 2 and the mounts 7. A rotation of the outer masses a and b around the axis of rotation $x_2$, $X_4$ and $x_6$ corresponds to an oscillation in the second natural mode. The mathematical formulation of the oscillatory pattern of this system can be derived with the aid of the second Lagrange equation as explained at the end of this description.

Shown below, in conclusion, are the energy balance and motion equations referred to further above.

Energy Balance

Kinetic Energy:

$$E = \frac{1}{2}m_{Ma}(\dot{x}_1+\dot{x}_2)^2 + \frac{1}{2}m_{Mb}(\dot{x}_1-\dot{x}_2)^2 + \frac{1}{2}m_{Mm}\dot{x}_1^2 + \quad (29)$$
$$\frac{1}{2}m_{Ta}(\dot{x}_3+\dot{x}_4)^2 + \frac{1}{2}m_{Tb}(\dot{x}_3-\dot{x}_4)^2 + \frac{1}{2}m_{Tm}\dot{x}_3^2 +$$
$$\frac{1}{2}m_{Aa}(\dot{x}_5+\dot{x}_6)^2 + \frac{1}{2}m_{Ab}(\dot{x}_5-\dot{x}_6)^2$$

Energy Dissipated Per Unit of Time:

$$D = \frac{1}{2}d_{Ma}(\dot{x}_1+\dot{x}_2-\dot{x}_5-\dot{x}_6)^2 + \frac{1}{2}d_{Md}(\dot{x}_1-\dot{x}_2-\dot{x}_5+\dot{x}_6)^2 + \quad (30)$$
$$\frac{1}{2}d_{Ta}(-\dot{x}_3-\dot{x}_4+\dot{x}_5+\dot{x}_6)^2 + \frac{1}{2}d_{Tb}(-\dot{x}_3+\dot{x}_4+\dot{x}_5-\dot{x}_6)^2 +$$
$$\frac{1}{2}d_{Aa}(\dot{x}_5+\dot{x}_6)^2 + \frac{1}{2}d_{Ab}(\dot{x}_5-\dot{x}_6)^2 + \frac{1}{2}d_m(\dot{x}_1-\dot{x}_3)^2$$

Potential Energy:

$$U = \frac{1}{2}c_{Ma}(x_1+x_2-x_5-x_6)^2 + \frac{1}{2}c_{Mb}(x_1-x_2-x_5+x_6)^2 + \quad (31)$$
$$\frac{1}{2}c_{Ta}(-x_3-x_4+x_5+x_6)^2 + \frac{1}{2}c_{Tb}(-x_3+x_4+x_5-x_6)^2 +$$
$$\frac{1}{2}c_{Aa}(x_5+x_6)^2 + \frac{1}{2}c_{Ab}(x_5-x_6)^2 + \frac{1}{2}c_m(x_1-x_3)^2$$

Motion Equations:

$$\frac{d}{dt}\left(\frac{\partial E}{\partial \dot{q}_n}\right) - \frac{\partial E}{\partial q_n} + \frac{\partial D}{\partial \dot{q}_n} + \frac{\partial U}{\partial q_n} = F_n \quad (32)$$

First natural mode translational movement of the measuring tube along the $x_1$ axis:

$(m_{Ma}+m_{Mb}+m_{Mm})\ddot{x}_1+(d_{Ma}+d_{Mb}+d_m)$
$\dot{x}_1+(c_{Ma}+c_{Mb}+c_m)x_1+(m_{Ma}-m_{Mb})\ddot{x}_2+(d_{Ma}-d_{Mb})$
$\dot{x}_2+(c_{Ma}-c_{Mb})x_2+(-d_m)\ddot{x}_3+(-c_m)x_3+(-d_{Ma}-d_{Mb})$
$\dot{x}_5+(-c_{Ma}-c_{Mb})x_5+(-d_{Ma}+d_{Mb})$
$\dot{x}_6+(-c_{Ma}+c_{Mb})x_6=F_1$ \quad (33)

Second natural mode rotation of the measuring tube around the $x_2$ axis:

$(m_{Ma}+m_{Mb})\ddot{x}_2+(d_{Ma}+d_{Mb})$
$\dot{x}_2+(c_{Ma}+c_{Mb})x_2+(m_{Ma}-m_{Mb})\ddot{x}_1+(d_{Ma}-d_{Mb})$
$\dot{x}_1+(c_{Ma}-c_{Mb})x_1+(-d_{Ma}+d_{Mb})$
$\dot{x}_5+(-c_{Ma}+c_{Mb})x_5+(-d_{Ma}-d_{Mb})$
$\dot{x}_6+(-c_{Ma}-c_{Mb})x_6=F_2$ \quad (34)

Translational movement of the support pipe along the $x_3$ axis:

$(m_{Ta}+m_{Tb}+m_{Tm})\ddot{x}_3+(d_{Ta}+d_{Tb}+d_m)$
$\dot{x}_3+(c_{Ta}+c_{Tb}+c_m)x_3+(-d_m)\dot{x}_1+(-c_m)x_1+(m_{Ta}-m_{Tb})$
$\ddot{x}_4+(d_{Ta}-d_{Tb})\dot{x}_4+(c_{Ta}-c_{Tb})x_4+(-d_{Ta}-d_{Tb})$
$\dot{x}_5+(-c_{Ta}-c_{Tb})x_5+(-d_{Ta}+d_{Tb})\dot{x}_6+(-c_{Ta}+c_{Tb})x_6=F_1$ \quad (35)

Rotation of the support pipe around the $x_4$ axis:

$(m_{Ta}+m_{Tb})\ddot{x}_4+(d_{Ta}+d_{Tb})\dot{x}_4+(c_{Ta}+c_{Tb})x_4+(m_{Ta}-m_{Tb})$
$\ddot{x}_3+(d_{Ta}-d_{Tb})\dot{x}_3+(c_{Ta}-c_{Tb})x_3+(-d_{Ta}+d_{Tb})$
$\dot{x}_5+(-c_{Ta}+c_{Tb})x_5+(-d_{Ta}-d_{Tb})$
$\dot{x}_6+(-c_{Ta}-c_{Tb})x_6\times-F_2$ \quad (36)

Translational movement along the $x_5$ axis:

$$(m_{Aa}+m_{Ab})\ddot{x}_5+(d_{Ma}+d_{Mb}+d_{Ta}+d_{Tb}+d_{Aa}+d_{Ab})$$
$$\dot{x}_5+(c_{Ma}+c_{Mb}+c_{Ta}+c_{Tb}+c_{Aa}+c_{Ab})x_5+(-d_{Ma}-d_{Mb})$$
$$\dot{x}_1+(-c_{Ma}-c_{Mb})x_1+(-d_{Ma}+d_{Mb})$$
$$\dot{x}_2+(-c_{Ma}-c_{Mb})x_2+(-d_{Ta}-d_{Tb})$$
$$\dot{x}_3+(-c_{Ta}-c_{Tb})x_3+(-d_{Ta}+d_{Tb})$$
$$\dot{x}_4+(-c_{Ta}+c_{Tb})x_4+(m_{Aa}-m_{Ab})$$
$$\ddot{x}_6+(d_{Ma}-d_{Mb}+d_{Ta}-d_{Tb}+d_{Aa}-d_{Ab})$$
$$\dot{x}_6+(c_{Ma}-c_{Mb}+c_{Ta}-c_{Tb}+c_{Aa}-c_{Ab})x_6=F_5 \quad (37)$$

Rotation around the $x_6$ axis:

$$(m_{Aa}+m_{Ab})\ddot{x}_6+(d_{Ma}+d_{Mb}+d_{Ta}+d_{Tb}+d_{Aa}+d_{Ab})$$
$$\dot{x}_6+(c_{Ma}+c_{Mb}+c_{Ta}+c_{Tb}+c_{Aa}+c_{Ab})x_6+(-d_{Ma}+d_{Mb})$$
$$\dot{x}_1+(-c_{Ma}+c_{Mb})x_1+(-d_{Ma}-d_{Mb})$$
$$\dot{x}_2+(-c_{Ma}-c_{Mb})x_2+(-d_{Ta}+d_{Tb})$$
$$\dot{x}_3+(-c_{Ta}+c_{Tb})x_3+(-d_{Ta}-d_{Tb})$$
$$\dot{x}_4+(-c_{Ta}-c_{Tb})x_4+(m_{Aa}-m_{Ab})$$
$$\ddot{x}_5+(d_{Ma}-d_{Mb}+d_{Ta}-d_{Tb}+d_{Aa}-d_{Ab})$$
$$\dot{x}_5+(c_{Ma}-c_{Mb}+c_{Ta}-c_{Tb}+c_{Aa}-c_{Ab})x_5=F_6 \quad (38)$$

What is claimed is:

1. A method for operating a mass flowmeter employing the Coriolis principle, said mass flowmeter incorporating a measuring tube through which flows a medium and which is stimulated into oscillating at a minimum of one frequency, whereupon the resulting oscillations of the measuring tube are detected and measured, wherein he viscosity of the medium flowing through the measuring tube is determined on the basis of the pressure drop along the measuring tube and said pressure drop is determined as a function of the dynamic pressure by applying the formula $$\Delta p = C_w \cdot P_s \frac{L}{d},$$

where $\Delta p$ represents the pressure drop along the measuring tube, $C_w$ is the coefficient of friction which in particular for laminar flows is derived via 64/Re with the Reynolds' number Re, $P_s$ is the dynamic pressure, L is the length of the measuring tube and d is the diameter of the measuring tube.

2. The method as in claim 1, wherein the dynamic pressure is indirectly determined via the mean velocity $\bar{v}$, preferably by applying the formula $$p_s = \frac{1}{2}\rho \cdot \bar{v},$$

where $\rho$ denotes the density of the medium flowing through the measuring tube.

3. The method as in claim 1 or 2 wherein the mathematical correlation between the coefficient of friction $C_w$ and the Reynolds' number Re that is provided for the determination of the viscosity of the medium flowing through the measuring tube is stored in a memory module of the mass flowmeter.

4. The method as in claim 1 or 2 wherein the viscosity is determined by applying the formula $$\eta = \frac{\bar{v}\rho d}{Re}.$$

5. The method as in claim 1 or 2, wherein the pressure drop along the measuring tube is determined by evaluating the detected oscillations of the measuring tube on the basis of a physical-mathematical model for the dynamics of the mass flowmeter.

6. The method as in claim 5, wherein the physical-mathematical model is suitable for describing the oscillations of the mass flowmeter upon stimulation of the measuring tube in at least one natural mode.

7. The method as in claim 6, wherein the physical-mathematical model takes into account the coupling between at least two natural modes of the oscillations of the measuring tube.

8. The method as in claim 5, wherein the physical-mathematical model reflects, in addition to the measuring tube, the effect of at least one other component of the mass flowmeter such as a support pipe and/or a suspension of the measuring tube in the mass flowmeter.

9. The method as in claim 8, wherein the physical-mathematical model reflects, in addition to the measuring tube, the effect of at least one other component of the mass flowmeter such as a support pipe and/or a suspension of the measuring tube in the mass flowmeter.

10. The method as in claim 8, wherein the temperature in the mass flowmeter is measured to allow the integration of the temperature dependence of the function of mass flowmeter components such as an osciallation generator for the measuring tube and/or an oscillation sensor for the measuring tube.

11. The method as in claim 8, wherein the temperature of the measuring tube is measured to allow temperature-related changes of the measuring tube geometry to be taken into account.

12. The method as in claim 8, wherein the pressure in the measuring tube is determined to allow pressure-related changes of the measuring tube geometry to be taken into account.

13. The method as in claim 4, wherein the physical-mathematical model takes into account the coupling between at least two natural modes of the oscillations of the measuring tube.

14. A method for operating a mass flowmeter employing the Coriolis principle, said mass flowmeter incorporating a measuring tube through which flows a medium and which is stimulated into oscillating at a minimum of one frequency, whereupon the resulting oscillations of the measuring tube are detected and measured, wherein the viscosity of the medium flowing through the measuring tube is determined on the basis of the pressure drop along the measuring tube, and wherein the pressure drop along the measuring tube is determined by evaluating the detected oscillations of the measuring tube on the basis of a physical mathematical model for the dynamics of the mass flowmeter.

15. The method as in claim 14, wherein a mathematical correlation between the coefficient of friction $C_w$ and the Reynolds' number Re is provided for the determination of the viscosity of the medium flowing through the measuring tube and is stored in a memory module of the mass flowmeter.

16. The method as in claim 14 or 15, wherein the physical-mathematical model is suitable for describing the oscillations of the mass flowmeter upon stimulation of the measuring tube in at least one natural mode.

* * * * *